(12) United States Patent
Begg et al.

(10) Patent No.: US 11,524,146 B2
(45) Date of Patent: Dec. 13, 2022

(54) METHODS AND DEVICES FOR TRANSCERVICAL TREATMENT OF ENDOMETRIAL CANCER AND HYPERPLASIA

(71) Applicant: Covidien LP, Mansfield, MA (US)

(72) Inventors: Nikolai D. Begg, Wellesley, MA (US); Chad A. Pickering, Woburn, MA (US); Jordan A. Whisler, Brookline, MA (US); Rebecca D. White, Kennett Square, PA (US)

(73) Assignee: COVIDIEN LP, Mansfield, MA (US)

( * ) Notice: Subject to any disclaimer, the term of this patent is extended or adjusted under 35 U.S.C. 154(b) by 208 days.

(21) Appl. No.: 16/818,334

(22) Filed: Mar. 13, 2020

(65) Prior Publication Data

US 2020/0289799 A1 Sep. 17, 2020

Related U.S. Application Data

(60) Provisional application No. 62/818,781, filed on Mar. 15, 2019.

(51) Int. Cl.
*A61M 25/10* (2013.01)
*A61M 25/00* (2006.01)
*A61L 29/16* (2006.01)

(52) U.S. Cl.
CPC .......... *A61M 25/1011* (2013.01); *A61L 29/16* (2013.01); *A61M 25/0026* (2013.01);
(Continued)

(58) Field of Classification Search
CPC .......... A61M 25/1011; A61M 25/0026; A61M 2025/1013; A61M 2025/105;
(Continued)

(56) References Cited

U.S. PATENT DOCUMENTS

| 4,182,328 A | 1/1980 | Bolduc et al. |
| 8,048,101 B2 | 11/2011 | Lee-Sepsick et al. |

(Continued)

OTHER PUBLICATIONS

International Search Report and Written Opinion for Application No. PCT/US2020/022658 dated Jul. 13, 2020.

*Primary Examiner* — Bhisma Mehta
*Assistant Examiner* — Phoebe Anne Staton
(74) *Attorney, Agent, or Firm* — Carter, DeLuca & Farrell LLP

(57) ABSTRACT

An infusion catheter includes a housing, a proximal shaft assembly, a first distal shaft assembly and a second distal shaft assembly. The housing has one or more inflation ports and one or more infusion ports. The proximal shaft assembly supports a first balloon. The first distal shaft assembly extends distally from the proximal shaft assembly and supports a first distal balloon. The second distal shaft assembly extends distally from the proximal shaft assembly and supports a second distal balloon. The first and second distal shaft assemblies define infusion openings in fluid communication with the one or more infusion ports. The infusion catheter may be inserted into a uterine cavity to occlude tubal ostia and an internal cervical OS of the uterine cavity for sealing the uterine cavity. A therapeutic agent may be delivered through the infusion catheter and into the sealed uterine cavity to treat the uterine cavity.

18 Claims, 5 Drawing Sheets

(52) U.S. Cl.
CPC ............... *A61M 2025/105* (2013.01); *A61M 2025/1013* (2013.01); *A61M 2025/1045* (2013.01); *A61M 2025/1052* (2013.01); *A61M 2210/1425* (2013.01)

(58) Field of Classification Search
CPC .. A61M 2025/1045; A61M 2025/1052; A61M 2210/1425; A61M 2025/1043; A61M 25/0105; A61M 25/0133; A61M 2025/0143; A61M 2025/1015; A61M 2210/1433; A61B 17/1204; A61B 17/42; A61B 17/12136; A61B 2017/4216
See application file for complete search history.

(56) References Cited

U.S. PATENT DOCUMENTS

| | | |
|---|---|---|
| 8,962,011 B2 | 2/2015 | Raspagliesi |
| 9,180,039 B2 | 11/2015 | Tal et al. |
| 9,510,088 B2 | 11/2016 | Tal et al. |
| 9,949,869 B2 | 4/2018 | Tjader et al. |
| 9,993,625 B2 | 6/2018 | Roth et al. |
| 2004/0138529 A1* | 7/2004 | Wiltshire ............ A61B 1/0055 600/144 |
| 2005/0240211 A1 | 10/2005 | Sporri et al. |
| 2008/0114286 A1 | 5/2008 | Hamel et al. |
| 2011/0056501 A1 | 3/2011 | Kortesuo et al. |
| 2011/0087109 A1 | 4/2011 | Swann |
| 2014/0214002 A1* | 7/2014 | Lieber ............... A61M 25/1011 604/509 |
| 2014/0378752 A1* | 12/2014 | Buster ................. A61B 50/13 600/33 |
| 2015/0230971 A1 | 8/2015 | Wildemeersch |

\* cited by examiner

METHODS AND DEVICES FOR TRANSCERVICAL TREATMENT OF ENDOMETRIAL CANCER AND HYPERPLASIA

CROSS REFERENCE TO RELATED APPLICATIONS

This application claims the benefit of U.S. Provisional Patent Application No. 62/818,781, filed Mar. 15, 2019, the entire contents of which are incorporated by reference herein.

TECHNICAL FIELD

This disclosure relates generally to the field of surgical instruments, and in particular, to infusion catheters for transcervical treatment of endometrial cancer and hyperplasia.

BACKGROUND

Endometrial cancer is the most common gynecologic malignancy. It is the fourth most common cancer in women in the United States after breast, lung, and colorectal cancers. Endometrial hyperplasia is characterized by a thickening of the endometrium that is more than the typical pre- and post-menstrual buildup of endometrial tissue. Low- to medium-risk endometrial hyperplasia can be treated with nonsurgical options. The mainstay of treatment for endometrial cancer and atypical endometrial hyperplasia is a total hysterectomy. Radiation and chemotherapy can also play a role in treatment.

SUMMARY

According to one aspect, this disclosure is directed to an infusion catheter. The infusion catheter includes a housing, a proximal shaft assembly, a first distal shaft assembly, and a second distal shaft assembly. The housing has one or more inflation ports and one or more infusion ports. The proximal shaft assembly supports a first balloon. The first distal shaft assembly extends distally from the proximal shaft assembly and supports a first distal balloon. The second distal shaft assembly extends distally from the proximal shaft assembly and supports a second distal balloon. The first and second distal shaft assemblies define infusion openings in fluid communication with the one or more infusion ports.

In embodiments, the first and second distal shaft assemblies may separate from one another at a distal end portion of the proximal shaft assembly to define a Y-shaped configuration.

In some embodiments, the balloons may be in fluid communication with the one or more inflation ports. The balloons may be selectively inflatable. The balloons may be selectively deflatable.

According to yet another aspect, a method for treating a uterine cavity includes inserting an infusion catheter into a uterine cavity, occluding tubal ostia and an internal cervical OS of the uterine cavity with the infusion catheter to seal the uterine cavity, and delivering a therapeutic agent through the infusion catheter and into the sealed uterine cavity to treat the uterine cavity.

The method may further include inflating distal balloons of the infusion catheter to occlude the tubal ostia.

The method may involve inflating a proximal balloon of the infusion catheter to occlude the internal cervical OS of the uterine cavity.

In aspects, delivering the therapeutic agent includes delivering a chemotherapeutic agent into the sealed uterine cavity to treat endometrial cancer.

In some aspects, delivering the therapeutic agent includes delivering a hormonal agent into the sealed uterine cavity to treat endometrial hyperplasia.

Other aspects, features, and advantages will be apparent from the description, the drawings, and the claims that follow.

BRIEF DESCRIPTION OF THE DRAWINGS

The accompanying drawings, which are incorporated in and constitute a part of this specification, illustrate embodiments of the disclosure and, together with the detailed description of the embodiments given below, serve to explain the principles of the disclosure.

DETAILED DESCRIPTION

Figure 1:
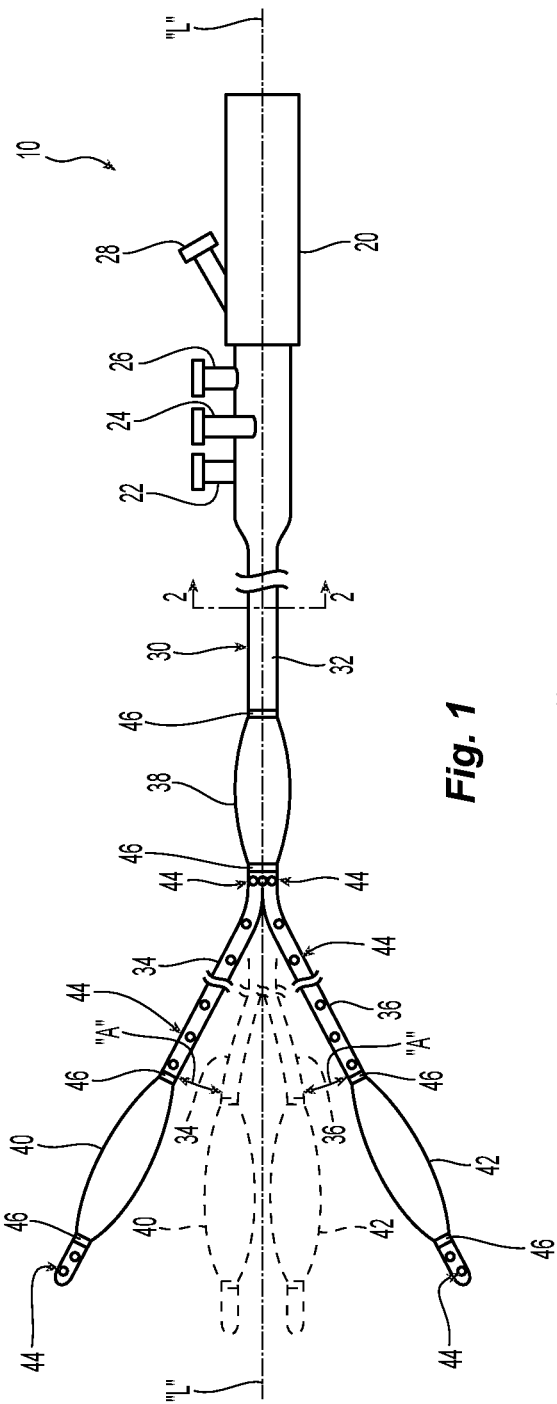
FIG. 1 is a perspective view of one embodiment of an infusion catheter in accordance with the principles of the disclosure.

Embodiments of the disclosed infusion catheters are described in detail with reference to the drawings, in which like reference numerals designate identical or corresponding elements in each of the several views. As commonly known, the term "clinician" refers to a doctor, a nurse, or any other care provider and may include support personnel. Further, as is used in the art, the term "distal" refers to a position, a direction, and/or a structure, which is farther from the user, and the term "proximal" refers to a position, a direction, and/or a structure, which is closer to the user. In addition, directional terms such as upper, lower, front, rear, top, bottom, up, down, right, left, and the like are used simply for convenience of description and are not intended to limit this disclosure.

Figure 2:
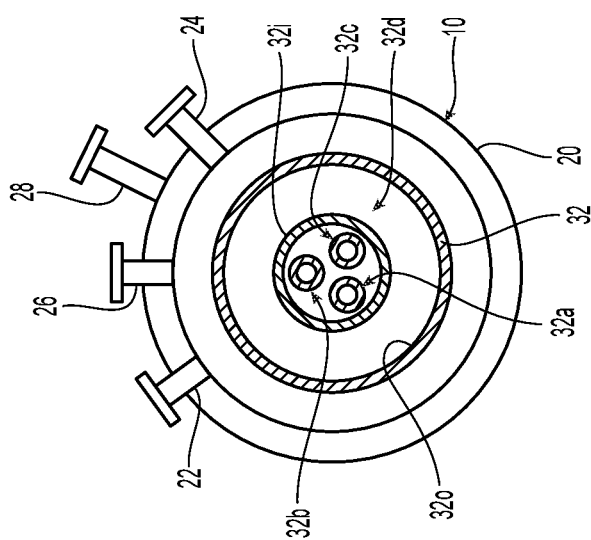
FIG. 2 is an enlarged, cross-sectional view as taken along section line 2-2 shown in FIG. 1.

Illustrated in FIGS. 1 and 2 is one embodiment of an infusion catheter 10. Infusion catheter 10 defines a longitudinal axis "L" and includes a housing 20 and an elongated shaft assembly 30 that extends distally from housing 20. Housing 20 includes a first inflation port 22, a second inflation port 24, and a third inflation port 26 that are configured to receive inflation fluid such as saline or any other suitable fluid. Housing 20 further includes an infusion port 28 configured to receive an infusion agent "IA" such as a chemotherapeutic or hormonal agent for direct delivery to a uterine cavity "C" (see FIG. 3C). For a more detailed description of a similar infusion catheter, one or more components of which may be included and/or modified for use with infusion catheter 10, reference can be made to U.S. Pat. No. 8,162,879, the entire contents of which are incorporated by reference herein.

Elongated shaft assembly 30 of infusion catheter 10 includes a proximal shaft assembly 32 that extends distally from housing 20 to a first distal shaft assembly 34 and a second distal shaft assembly 36. Proximal shaft assembly 32 includes an outer tube 32o and an inner tube 32i that is disposed within outer tube 32o and may be concentric with outer tube 32o. Inner tube 32i supports a first inflation conduit 32a that is disposed in fluid communication with first inflation port 22 of housing 20, a second inflation conduit 32b that is disposed in fluid communication with second inflation port 24 of housing 20, and a third inflation conduit 32c that is disposed in fluid communication with third inflation port 26 of housing 20. Between outer tube 32o and inner tube 32i of proximal shaft assembly 32 is an infusion lumen 32d disposed in fluid communication with infusion port 28 of housing 20. Supported on an outer surface of outer tube 32o of proximal shaft assembly 32 is a proximal balloon 38 that is disposed in fluid communication with first inflation conduit 32a to enable proximal balloon 38 to be selectively inflated from a deflated position (FIG. 3A) to an inflated position (FIG. 3B) and/or vice versa. Proximal balloon 38 is configured to be received in an internal cervical OS "COS" for occluding the internal cervical OS "COS."

First and second distal shaft assemblies 34, 36 of elongated shaft assembly 30 separate at a distal end portion of proximal shaft assembly 32 of elongated shaft assembly 30 to define a Y-shape. First distal shaft assembly 34 supports a first distal balloon 40 on a distal end portion of first distal shaft assembly 34. Second distal shaft assembly 36 supports a second distal balloon 42 on a distal end portion of second distal shaft assembly 36. First and second distal shaft assemblies 34, 36 may be formed of a flexible material. In some embodiments, first and second distal shaft assemblies 34, 36 may be formed of shape memory material. As indicated by arrows "A," first and second distal shaft assemblies 34, 36 are configured to move between a closed position (e.g., phantom illustration in FIG. 1), which may be in parallel relation to the longitudinal axis "L" of infusion catheter 10, and an open position, in which first and second distal shaft assemblies 34, 36 are angled away from (e.g., transverse to) the longitudinal axis "L" (e.g., the non-phantom illustration seen in FIG. 1). First and second distal balloons 40, 42 of first and second distal shaft assemblies 34, 36 are configured to be received in tubal ostia "TO" (e.g., openings of fallopian tubes) for selectively occluding the tubal ostia "TO." In particular, first and second distal balloons 40, 42 are configured for selective inflation from a deflated position (FIG. 3A) to an inflated position (FIG. 3B) and/or vice versa.

Infusion openings 44 are defined in outer surfaces of first and second distal shaft assemblies 34, 36, along lengths thereof, and/or a distal portion of proximal shaft assembly 32. Infusion openings 44 may be positioned in any suitable arrangement to enable application of the infusion agent "IA" to the uterine cavity "C," or portions thereof. As can be appreciated, any number of infusion openings 44 can have any suitable shape, size, configuration and/or pattern. Infusion openings 44 are disposed in fluid communication with infusion lumen 32d, which may extend through first and second distal shaft assemblies 34, 36.

Figure 3A:
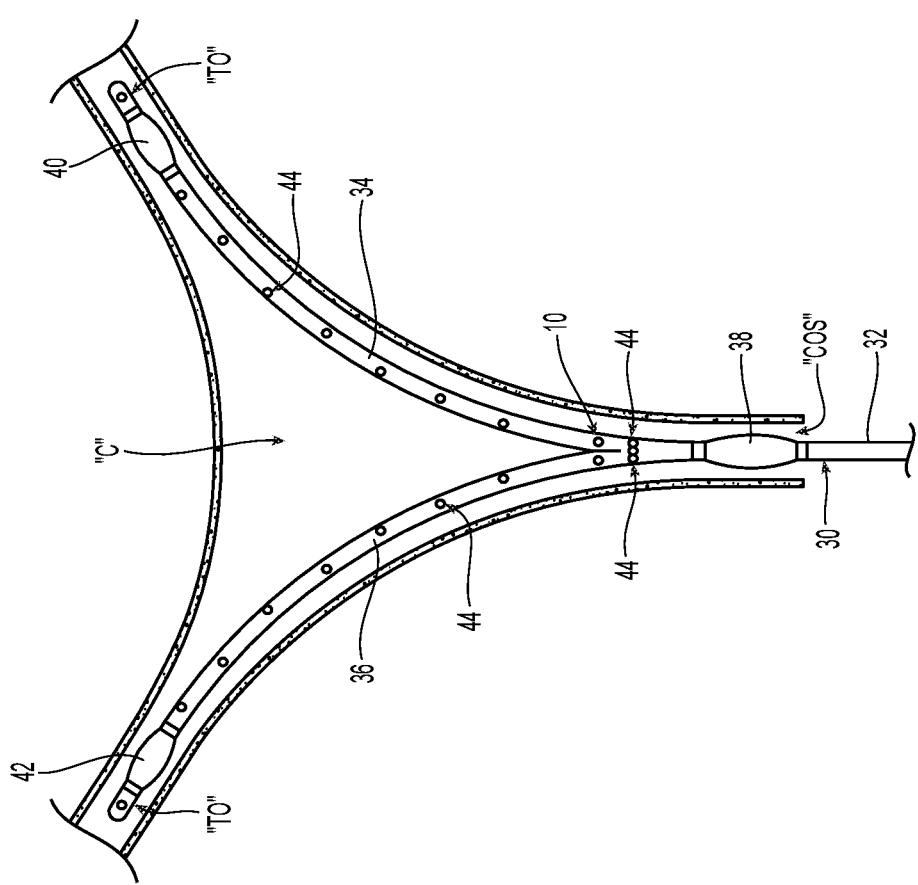
FIGS. 3A-3C are progressive views illustrating the infusion catheter of FIG. 1 being used to apply treatment within a uterine cavity.
Figure 3B:
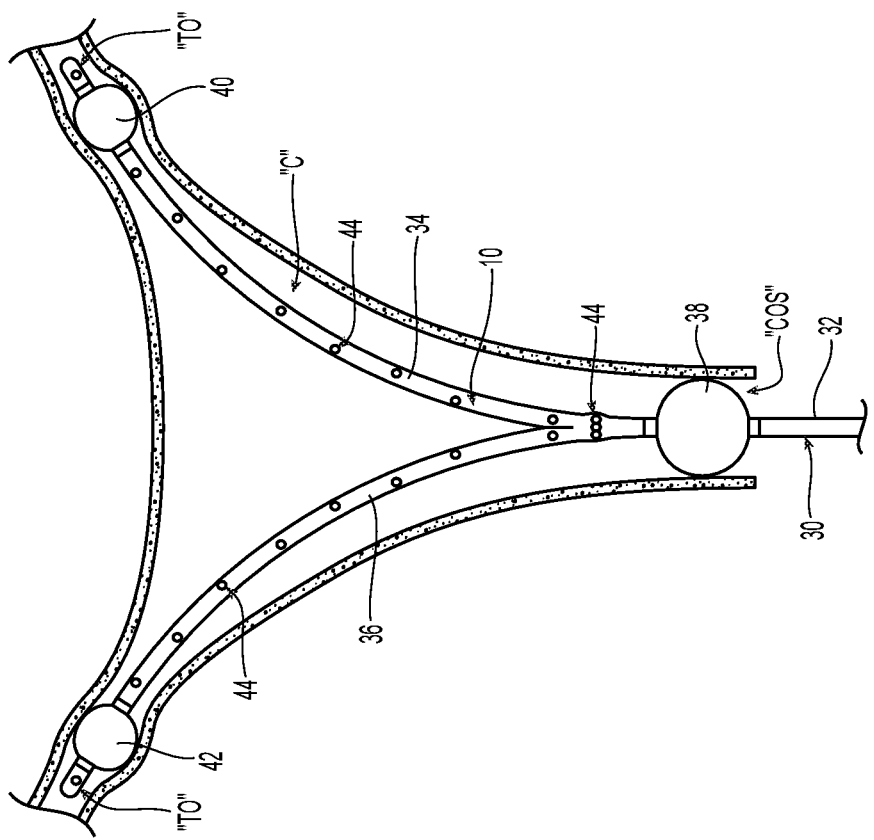
Figure 3C:
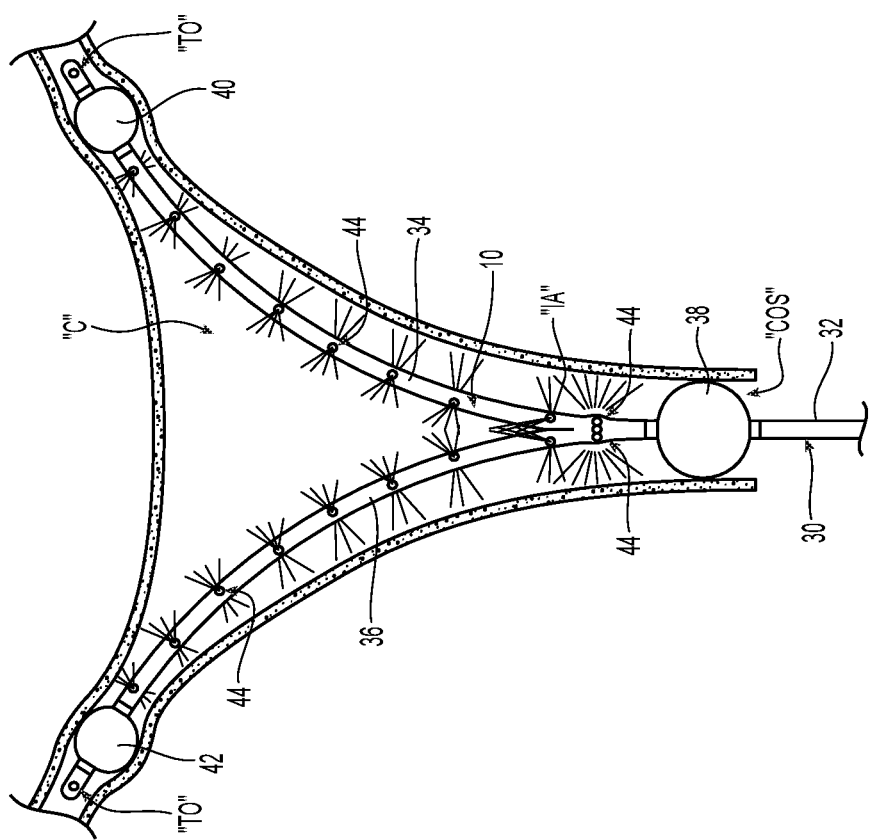

With reference to FIGS. 3A-3C, in order to treat, for example, endometrial cancer or atypical endometrial hyperplasia, infusion catheter 10 can be inserted into a uterine cavity "C," transcervically (e.g., across/through internal cervical OS "COS"), and advanced distally so that first and second distal balloons 40, 42 of distal shaft assemblies 34, 36, respectively, are disposed in the tubal ostia "TO" of the uterine cavity "C." As illustrated in FIG. 1, first and second distal shaft assemblies 34, 36 are configured to pivot or curve away from longitudinal axis "L" and each other, as indicated by arrows "A." For instance, as seen in FIG. 3A, first and second distal shaft assemblies 34, 36 may be formed of a material that is biased toward an abaxial position relative to longitudinal axis "L" so that distal advancement of first and second distal balloons 40, 42 enables first distal balloon 40 to be disposed in a first tubal ostium "TO" and second distal balloon 42 to be disposed in a second tubal ostium "TO." Further, with first and second distal balloons 40, 42 disposed in the tubal ostia "TO," proximal balloon 38 of infusion catheter 10 is disposed within internal cervical OS "COS." Proximal balloon 38 can be inflated to occlude internal cervical OS "COS" and first and second distal balloons 40, 42 can be inflated to occlude the tubal ostia "TO." Once balloons 38, 40, 42 are all inflated, all openings into the uterine cavity "C" are sealed. With the uterine cavity "C" sealed, infusion agent "IA" can be delivered or dispensed into uterine cavity "C" through infusion openings 44. Balloons 38, 40, 42 can have markers 46 supported on opposite ends thereof as delineated in FIG. 1. After delivery of infusion agent "IA," balloons 38, 40, 42 can be deflated and infusion catheter 10 can be removed from the uterine cavity "C."

Figure 4:
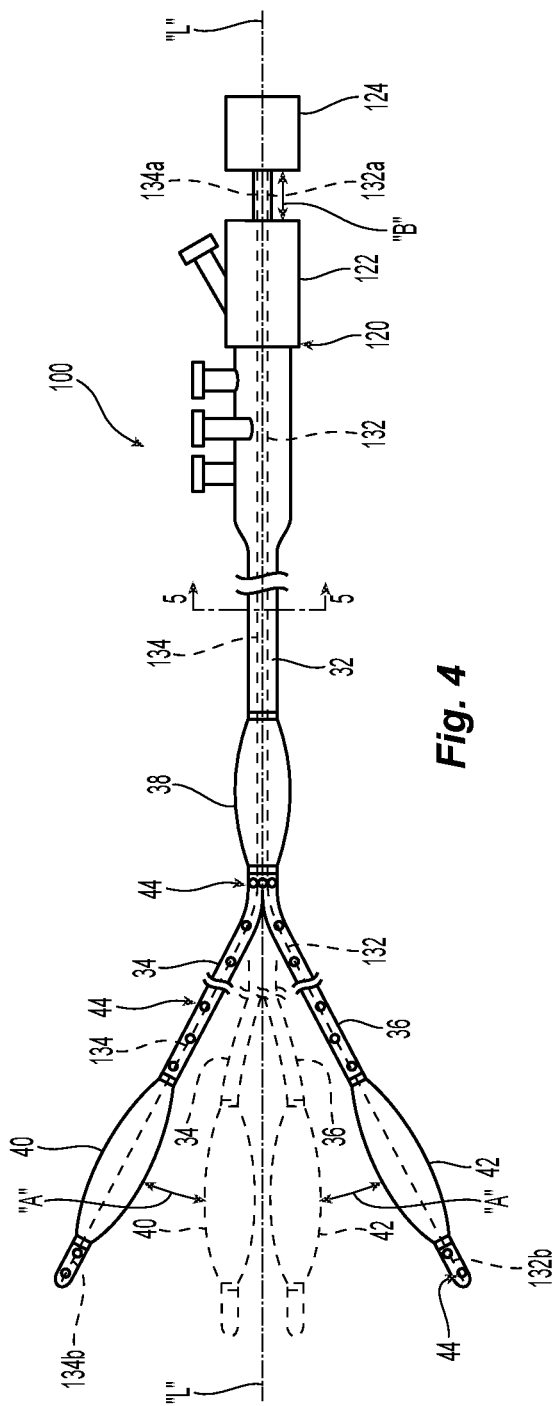
FIG. 4 is a perspective view of another embodiment of an infusion catheter in accordance with the principles of the disclosure.
Figure 5:
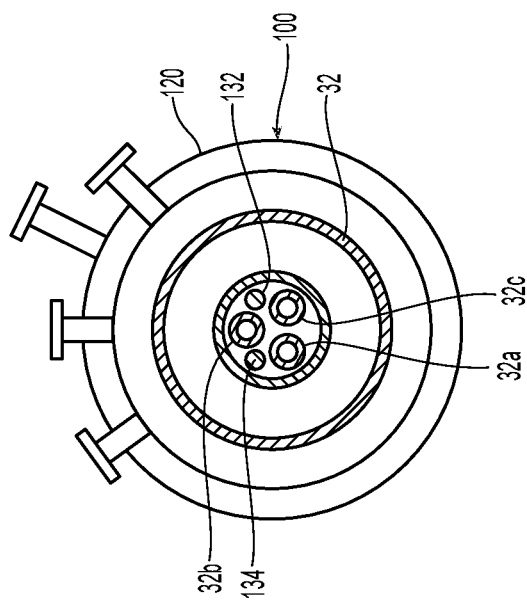
FIG. 5 is an enlarged, cross-sectional view as taken along section line 5-5 shown in FIG. 4.

As illustrated in FIGS. 4 and 5, another embodiment of an infusion catheter 100, which is similar to infusion catheter 100, includes a housing assembly 120 has a stationary housing 122 and a movable housing 124 that is selectively movable (e.g., axially) relative to stationary housing 122, for instance, between distal and proximal positions, as indicated by arrows "B." In particular, infusion catheter 100 further includes a first cable 132 and a second cable 134. First cable 132 includes a proximal end portion 132a coupled to movable housing 124 and a second end portion 132b coupled to a distal end portion of first distal shaft assembly 34. Second cable 134 includes a proximal end portion 134a coupled to movable housing 124 and a distal end portion 134b coupled to a distal end portion of second distal shaft assembly 36. Movement of movable housing 124 between the distal and proximal positions enables first and second distal shaft assemblies 34, 36 to move (or pivot) relative to longitudinal axis "L" and one another. For instance, similar to first and second distal shaft assemblies 34, 36 of infusion catheter 10, first and second distal shaft assemblies 34, 36 of infusion catheter 100 move between a closed or approximated position (shown in phantom), in which first and second distal shaft assemblies 34, 36 are adjacent to one another, and an open position, in which first and second distal shaft assemblies 34, 36 are curved away from one another and the longitudinal axis "L" for positioning within opposite tubal ostia "TO" (see FIG. 3C).

In some embodiments, movable housing 124 may be spring biased relative to the stationary housing 122 to maintain first and distal shaft assembly 34, 36 in the open position and/or the closed position.

In some embodiments, the disclosed housing assemblies may include any number of inflation ports (e.g., two or even a single inflation port) that is configured to simultaneously, and/or successively, inflate any two, or even all three balloons. In certain embodiments, the disclosed housing assemblies may include any number of infusion ports, for example, to deliver different infusion agents to the uterine cavity. Further, although the disclosed inflation conduits are illustrated as independent of one another, in some embodiments, two or more of the inflation conduits can be networked together to form a plexus of conduits.

As can be appreciated, securement of any of the components of the presently disclosed apparatus can be effectuated using known securement techniques such welding, crimping, gluing, fastening, etc.

The various embodiments disclosed herein may also be configured to work with robotic surgical systems and what is commonly referred to as "Telesurgery." Such systems employ various robotic elements to assist the clinician and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of clinicians may prep the patient for surgery and configure the robotic surgical system with one or more of the instruments disclosed herein while another clinician (or group of clinicians) remotely controls the instruments via the robotic surgical system. As can be appreciated, a highly skilled clinician may perform multiple operations in multiple locations without leaving his/her remote console which can be both economically advantageous and a benefit to the patient or a series of patients. For a detailed description of exemplary medical work stations and/or components thereof, reference may be made to U.S. Pat. No. 8,828,023, and PCT Application Publication No. WO2016/025132, the entire contents of each of which are incorporated by reference herein.

Persons skilled in the art will understand that the structures and methods specifically described herein and illustrated in the accompanying figures are non-limiting exemplary embodiments, and that the description, disclosure, and figures should be construed merely as exemplary of particular embodiments. It is to be understood, therefore, that this disclosure is not limited to the precise embodiments described, and that various other changes and modifications may be effected by one skilled in the art without departing from the scope or spirit of this disclosure. Additionally, it is envisioned that the elements and features illustrated or described in connection with one exemplary embodiment may be combined with the elements and features of another without departing from the scope of this disclosure, and that such modifications and variations are also intended to be included within the scope of this disclosure. Indeed, any combination of any of the disclosed elements and features is within the scope of this disclosure. Accordingly, the subject matter of this disclosure is not to be limited by what has been particularly shown and described.

What is claimed:

1. An infusion catheter, comprising:
    a housing having at least one inflation port and at least one infusion port, the housing including a movable portion and stationary portion;
    a proximal shaft assembly supporting a first balloon and defining a longitudinal axis;
    a first distal shaft assembly extending distally from the proximal shaft assembly and supporting a first distal balloon, the first distal shaft assembly having a first cable secured to the first distal shaft assembly; and
    a second distal shaft assembly extending distally from the proximal shaft assembly and supporting a second distal balloon, the first and second distal shaft assemblies defining infusion openings in fluid communication with the at least one infusion port, the second distal shaft assembly having a second cable secured to the second distal shaft assembly, the first and second cables being movable in opposite directions relative to the longitudinal axis in response to movement of the movable portion relative to the stationary portion, wherein movement of the movable portion in a first direction causes the first and second cables to draw the first and second distal shaft assemblies away from one another and the longitudinal axis to selectively position the first and second distal shaft assemblies in an open position in which the first and second distal balloons are configured to be disposed within opposite tubal ostia of a patient.

2. The infusion catheter of claim 1, wherein the first and second distal shaft assemblies separate from one another at a distal end portion of the proximal shaft assembly to define a Y-shaped configuration in the open position.

3. The infusion catheter of claim 2, wherein the first balloon, the first distal balloon, and/or the second distal balloon are in fluid communication with the at least one inflation port.

4. The infusion catheter of claim 3, wherein the first balloon, the first distal balloon, and/or the second distal balloon are selectively inflatable.

5. The infusion catheter of claim 4, wherein the first balloon, the first distal balloon, and/or the second distal balloon are selectively deflatable.

6. A method for treating a uterine cavity, the method comprising:
    inserting the infusion catheter of claim 1 into a uterine cavity of the patient;
    occluding tubal ostia and an internal cervical OS of the uterine cavity with the infusion catheter to seal the uterine cavity; and
    delivering a therapeutic agent through the infusion catheter and into the sealed uterine cavity to treat the uterine cavity.

7. The method of claim 6, further comprising inflating the first and second distal balloons of the infusion catheter to occlude the tubal ostia.

8. The method of claim 7, further comprising inflating the first balloon of the infusion catheter to occlude the internal cervical OS of the uterine cavity.

9. The method of claim 6, wherein delivering the therapeutic agent includes delivering a chemotherapeutic agent into the sealed uterine cavity to treat endometrial cancer.

10. The method of claim 6, wherein delivering the therapeutic agent includes delivering a hormonal agent into the sealed uterine cavity to treat endometrial hyperplasia.

11. The infusion catheter of claim 1, wherein the first distal shaft assembly includes a distal end that extends distally beyond the first distal balloon.

12. The infusion catheter of claim 11, wherein the second distal shaft assembly includes a distal end that extends distally beyond the second distal balloon.

13. The infusion catheter of claim 11, wherein the distal end of the first distal shaft assembly has a blunt tip.

14. The infusion catheter of claim 11, wherein the movable portion is axially translatable relative to the stationary portion between proximal and distal positions.

15. The infusion catheter of claim 1, wherein the infusion catheter is robotically controlled.

16. The infusion catheter of claim 1, wherein at least one of the infusion openings is defined in the first distal shaft assembly proximal to the first distal balloon.

17. The infusion catheter of claim 1, wherein at least one of the infusion openings is defined in the first distal shaft assembly distal to the first distal balloon.

18. The infusion catheter of claim 1, wherein in an inflated state, the first distal balloon defines a circular cross-section about a circumference of the first distal shaft assembly.

\* \* \* \* \*